(12) United States Patent
Alvarez et al.

(10) Patent No.: US 10,529,073 B2
(45) Date of Patent: *Jan. 7, 2020

(54) VIRTUAL MODEL OF ARTICULATION FROM INTRA-ORAL SCANS

(71) Applicant: 3M INNOVATIVE PROPERTIES COMPANY, St. Paul, MN (US)

(72) Inventors: Alberto Alvarez, Madrid (ES); Eric S. Hansen, Arden Hills, MN (US); Steven C. Demlow, Mendota Heights, MN (US); Richard E. Raby, Lino Lakes, MN (US)

(73) Assignee: 3M INNOVATION PROPERTIES COMPANY, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/379,907

(22) Filed: Apr. 10, 2019

(65) Prior Publication Data

US 2019/0236785 A1    Aug. 1, 2019

Related U.S. Application Data

(63) Continuation of application No. 15/196,631, filed on Jun. 29, 2016, now Pat. No. 10,304,190.

(51) Int. Cl.
*G06T 7/00* (2017.01)
*A61C 11/00* (2006.01)
(Continued)

(52) U.S. Cl.
CPC ............ *G06T 7/0016* (2013.01); *A61C 7/002* (2013.01); *A61C 9/0053* (2013.01); *A61C 11/00* (2013.01);
(Continued)

(58) Field of Classification Search
CPC ... A61C 11/00; A61C 19/05; A61C 2007/004; A61C 7/002; A61C 9/0053; G06T 19/20; G06T 2207/10016; G06T 2207/30036; G06T 2219/2004; G06T 2219/2016; G06T 7/0016; G06T 7/344; G06T 7/74; G06T 7/75

See application file for complete search history.

(56) References Cited

U.S. PATENT DOCUMENTS 6,152,731 A    11/2000    Jordan et al.
6,322,359 B1   11/2001    Jordan et al.
(Continued)

FOREIGN PATENT DOCUMENTS

WO    WO 01/80761    11/2001
WO    WO 2012/100203    7/2012
(Continued)

*Primary Examiner* — Nirav G Patel

(57) ABSTRACT

A method for determining virtual articulation from dental scans. The method includes receiving digital 3D models of a person's maxillary and mandibular arches, and digital 3D models of a plurality of different bite poses of the arches. The digital 3D models of the maxillary and mandibular arches are registered with the bite poses to generate transforms defining spatial relationships between the arches for the bite poses. Based upon the digital 3D models and transforms, the method computes a pure rotation axis representation for each bite pose of the mandibular arch with respect to the maxillary arch. The virtual articulation can be used in making restorations or for diagnostic purposes.

19 Claims, 17 Drawing Sheets

(51) Int. Cl.
*G06T 7/73* (2017.01)
*G06T 19/20* (2011.01)
*G06T 7/33* (2017.01)
*A61C 7/00* (2006.01)
*A61C 9/00* (2006.01)
*A61C 19/05* (2006.01)

(52) U.S. Cl.
CPC ............... *G06T 7/344* (2017.01); *G06T 7/74* (2017.01); *G06T 7/75* (2017.01); *G06T 19/20* (2013.01); *A61C 19/05* (2013.01); *A61C 2007/004* (2013.01); *G06T 2207/10016* (2013.01); *G06T 2207/30036* (2013.01); *G06T 2219/2004* (2013.01); *G06T 2219/2016* (2013.01)

(56) References Cited

U.S. PATENT DOCUMENTS

| | | | |
|---|---|---|---|
| 6,582,229 | B1 | 6/2003 | Miller et al. |
| 6,948,936 | B2 | 9/2005 | Miller et al. |
| 7,347,690 | B2 | 3/2008 | Jordan et al. |
| 7,452,207 | B2 | 11/2008 | Miller et al. |
| 7,551,760 | B2 | 6/2009 | Scharlack et al. |
| 7,605,817 | B2 | 10/2009 | Zhang et al. |
| 7,698,014 | B2 | 4/2010 | Dunne et al. |
| 7,813,591 | B2 | 10/2010 | Paley et al. |
| 7,840,042 | B2 | 11/2010 | Kriveshko et al. |
| 7,912,257 | B2 | 3/2011 | Paley et al. |
| 7,956,862 | B2 | 6/2011 | Zhang et al. |
| 8,199,988 | B2 | 6/2012 | Marshall et al. |
| 8,215,956 | B2 | 7/2012 | Dunne et al. |
| 8,262,388 | B2 | 9/2012 | Dunne et al. |
| 8,374,714 | B2 | 2/2013 | Dunne et al. |
| 8,454,365 | B2 | 6/2013 | Boerjes et al. |
| 8,738,340 | B2 | 5/2014 | Dunne et al. |
| 8,866,883 | B2 | 10/2014 | Rohaly et al. |
| 8,897,902 | B2 | 11/2014 | See et al. |
| 9,084,653 | B2 | 7/2015 | Jordan et al. |
| 9,125,712 | B2 | 9/2015 | Kraemer et al. |
| 9,208,531 | B2 | 12/2015 | Boerjes et al. |
| 9,262,864 | B2 | 2/2016 | Rohaly et al. |
| 2002/0094509 | A1 | 7/2002 | Durbin et al. |
| 2003/0198917 | A1 | 10/2003 | Miller et al. |
| 2005/0196724 | A1 | 9/2005 | Miller et al. |
| 2007/0207441 | A1 | 9/2007 | Lauren |
| 2012/0231421 | A1 | 9/2012 | Boerjes et al. |
| 2013/0066598 | A1 | 3/2013 | Fisker et al. |
| 2014/0372084 | A1 | 12/2014 | Cowbum |
| 2016/0004811 | A1 | 1/2016 | Somasundaram et al. |
| 2016/0162631 | A1 | 6/2016 | Klein |

FOREIGN PATENT DOCUMENTS

| | | |
|---|---|---|
| WO | WO 2014/060595 | 4/2014 |
| WO | WO 2014/139078 | 9/2014 |
| WO | WO 2015/123759 | 8/2015 |
| WO | WO 2016/055932 | 4/2016 |

VIRTUAL MODEL OF ARTICULATION FROM INTRA-ORAL SCANS

BACKGROUND

Digital dentistry is a growing trend with an increasing number of dentists relying on digital impressioning systems. These systems use an intra-oral scanning camera, or scanning of a traditional physical impression, and an associated processing system to generate a digital three-dimensional (3D) model of patients' teeth.

The digital 3D models can then be used to make prosthodontic restorations and for advanced diagnostics such as detecting tooth wear. Accurate articulation is a key factor in making such restorations and for the diagnostics. Current data acquisition for mechanical articulation is time consuming and requires expensive analog devices. In particular, the current technique involves a manual process using a face bow and lab articulator to capture mandibular articulation data for complex rehabilitations.

Accordingly, a need exists for a digital replacement to the current manual process for obtaining articulation information.

SUMMARY

A method for determining virtual articulation from dental scans, consistent with the present invention, includes receiving digital 3D models of a person's maxillary and mandibular arches, and receiving digital 3D models of a plurality of different bite poses of the maxillary and mandibular arches. The method determines a virtual articulation model, based upon the digital 3D models of the plurality of different bite poses, including a digital representation of a pure rotation axis of the mandibular arch with respect to the maxillary arch for each articulation motion corresponding to a bite pose.

BRIEF DESCRIPTION OF THE DRAWINGS

The accompanying drawings are incorporated in and constitute a part of this specification and, together with the description, explain the advantages and principles of the invention. In the drawings.

DETAILED DESCRIPTION

The use of digital 3D models in the dental market is becoming more prevalent. These models can either be acquired directly in vivo using an intra-oral scanner, Cone Beam Computed Tomography (CBCT) scanning (i.e., 3D X-ray), or Magnetic Resonance Imaging (MRI), for example; or they can be acquired indirectly by scanning an impression of the teeth or a casting made from an impression of the teeth. Some examples of indirect data acquisition methods include, but are not limited to, industrial Computed Tomography (CT) scanning (i.e., 3D X-ray), laser scanning, and patterned light scanning. The digital 3D models can be used for varied clinical tasks including treatment planning, crown and implant preparation, prosthodontic restorations, orthodontic setup design, orthodontic appliance design, and in diagnostic aides, for example to assess or visually illustrate tooth wear.

Overview

Embodiments of the present invention calculate a virtual model of mandibular articulation from several extreme bite scans captured with an intraoral scanner. Since the virtual model permits reproducing any possible movement of the patient's mandible relative to the maxilla, this invention can facilitate, for example, prosthesis design, orthodontic setup design, wear facets identification, facets root cause identification, tooth wear prediction, dynamic occlusion design and adjustment (lateral and protrusive interferences avoidance, premature contacts elimination) and other advanced diagnoses, predictions and treatment plans. A key innovation is the calculation of mandibular motion from tooth surface data available via intra-oral scanners.

Figure 1:
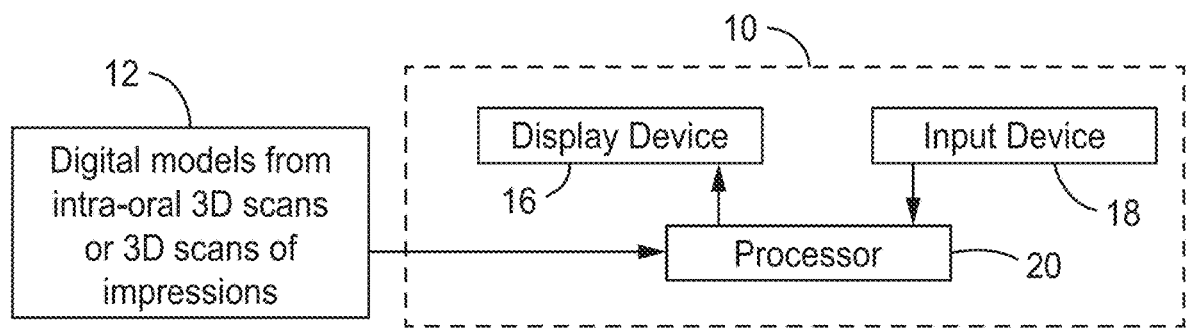
FIG. 1 is a diagram of a system for generating virtual articulation using digital 3D models from intra-oral scans.
Figure 2:
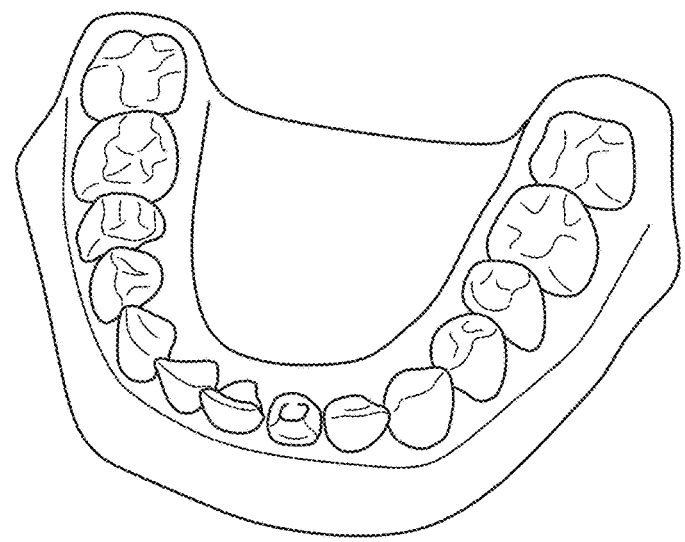
FIG. 2 illustrates a 3D model of teeth from intra-oral scans.

FIG. 1 is a diagram of a system 10 for generating virtual articulation using digital 3D models from intra-oral scans. System 10 includes a processor 20 receiving digital 3D models of teeth or other intra-oral structures (12) from intra-oral 3D scans or scans of impressions or castings of teeth. System 10 can also include an electronic display device 16 for displaying digital 3D models from scans of intra-oral structures and an input device 18 for receiving user commands or other information. An example of a digital 3D model of a patient's teeth from a scan is shown in FIG. 2. Systems to generate digital 3D images or models based upon image sets from multiple views are disclosed in U.S. Pat. Nos. 7,956,862 and 7,605,817, both of which are incorporated herein by reference as if fully set forth. These systems can use an intra-oral scanner to obtain digital images from multiple views of teeth or other intra-oral structures, and those digital images are processed to generate a digital 3D model or scan representing the scanned teeth or other intra-oral structure. The 3D models or scans can be implemented as, for example, a polygonal mesh or point cloud representing the surface of the scanned object or intra-oral structure.

Intra-oral structures include dentition, and more typically human dentition, such as individual teeth, quadrants, full arches, pairs of arches which may be separate or in occlusion of various types, soft tissue (e.g., gingival and mucosal surfaces of the mouth, or perioral structures such as the lips, nose, cheeks, and chin), and the like, as well as bones and any other supporting or surrounding structures. Intra-oral structures can possibly include both natural structures within a mouth and artificial structures such as dental objects (e.g., prosthesis, implant, appliance, restoration, restorative component, or abutment).

System 10 can be implemented with, for example, a desktop, notebook, or tablet computer. System 10 can receive the 3D scans locally or remotely via a network. Display device 16 can be implemented with any electronic display, for example a Cathode Ray Tube (CRT), a liquid crystal display (LCD), light emitting diode (LED) display, or organic light emitting diode (OLED) display. Input device 18 can be implemented with any device for entering information or commands, for example a keyboard, microphone, cursor-control device, or touch screen. The components of system 10 may also be combined, e.g., a tablet computer can incorporate the processor, display and touch screen input devices into a single unit.

Figure 3:
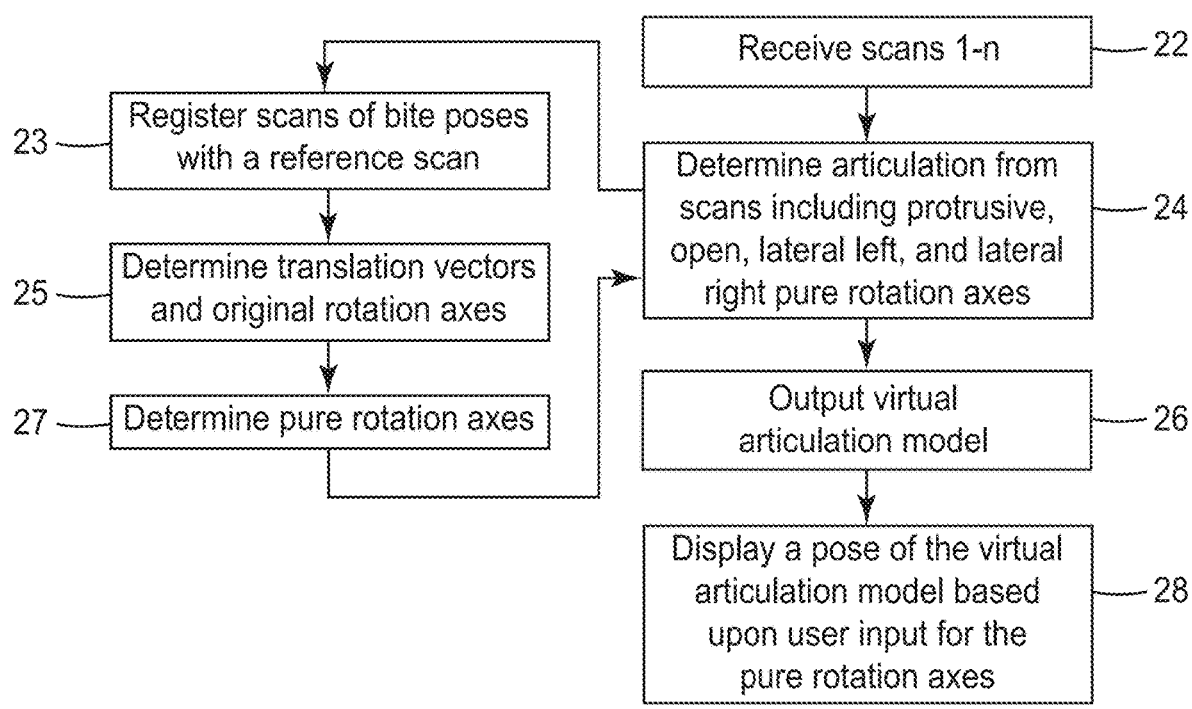
FIG. 3 is a flow chart representing determination of virtual articulation from intra-oral scans.

FIG. 3 is a flow chart representing a method for determining virtual articulation from intra-oral scans. This method includes, as further explained below, receiving digital 3D models or scans 1-n (step 22), determining articulation from the scans including protrusive (and optionally retrusive), open, lateral left, and lateral right pure rotation axes (step 24), outputting a virtual articulation model representing the movement of a person's mandible (step 26), and displaying a pose of the virtual articulation model based upon user input for the pure rotation axes or other types of input (step 28). The step 24 for determining articulation includes, as further explained below, registering scans of bite poses with a reference scan (step 23), determining translation vectors and original rotation axes (step 25), and determining pure rotation axes from the translation vectors and original rotation axes (step 27). This method can be implemented in software or firmware modules for execution by a processor such as processor 20, and the method can possibly be implemented using cloud computing. The virtual articulation model can be displayed on a display device such as display device 16, and a user may interact with the virtual articulation model via display device 16 and input device 18.

Figure 4:
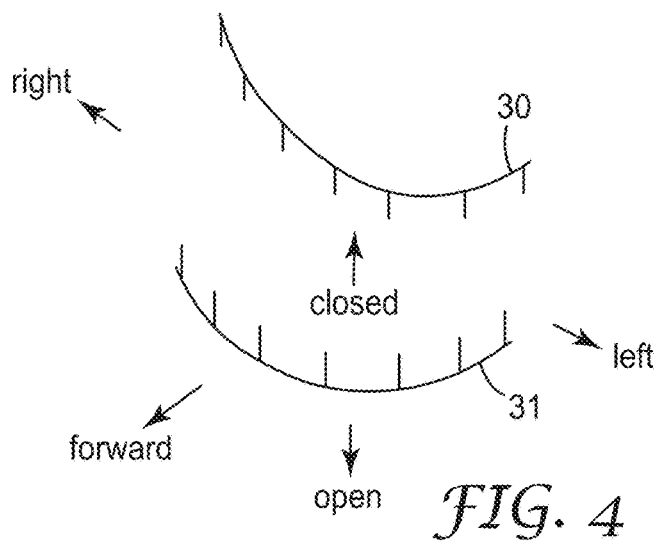
FIG. 4 illustrates bite poses for scans to generate virtual articulation.
Figure 5:
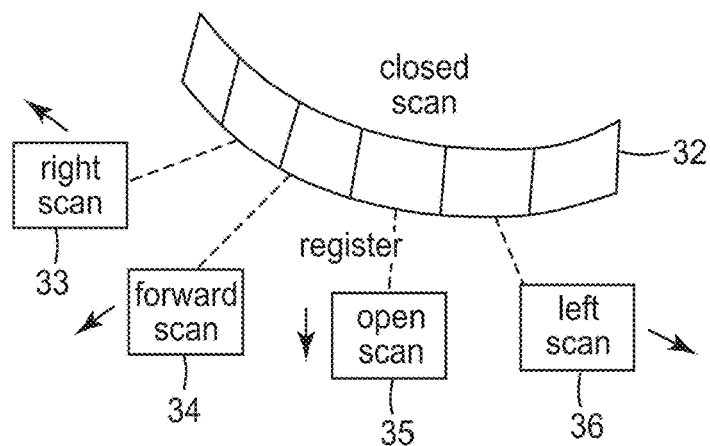
FIG. 5 illustrates registering the scans of bite poses to a reference scan.

The inputs to the method are a mandible scan, maxilla scan, and the following five bite pose scans: closed (centric/maximum intercuspation); open; forward or protrusive (and optionally retrusive); lateral left; and lateral right. FIG. 4 illustrates these bite poses of a mandibular (lower) arch 31 position with respect to a maxillary (upper) arch 30. The method finds the best fit registrations of these mandibular and maxillary arches to each of the five bite scans, establishing the relative relationship between the mandible and maxilla for each. FIG. 5 illustrates registering the scans of bite poses to a reference scan. In particular, and in this example, a closed bite scan 32, corresponding with a scan of maxillary and mandibular arches 30 and 31 in the closed position, is used as the reference scan, and the scans of the bite positions, right scan 33, forward scan 34, open scan 35, and left scan 36, are each registered with closed scan 32. Aside from closed scan 32, other scans can be used as the reference scan for the registration.

Using the maxilla as a fixed reference coordinate system, the method transforms these relative relationships into a shared coordinate system to attain transforms describing the extreme mandibular pose for each individual type of articulation relative to the closed pose, in particular closed to open, closed to protrusive, closed to lateral left, and closed to lateral right. Various forms of interpolation of the mandible position and orientation between the closed and respective bite pose, reflecting the mandible motion to attain that specific pose, are then possible. The overall mandibular motion in the virtual articulation model can then be expressed as composite transforms of the four individual articulation transforms at various stages of interpolation, limiting the interpolations according to physical anatomical constraints. Aside from extreme mandibular poses to the limits of those pose positions, other mandibular poses having a significant displacement, or at least sufficient displacement, to generate the virtual articulation can be used.

The movement of the mandible from the closed pose to any of the other poses can be described, for each pose, as the combination of a rotation matrix (the composite of three rotations around the coordinate axes x, y, z) and a translation vector of the origin of coordinates. This combination (rotation plus translation vector) is usually called a "3D transformation matrix" or more narrowly a "rigid body transform."

Figure 6:
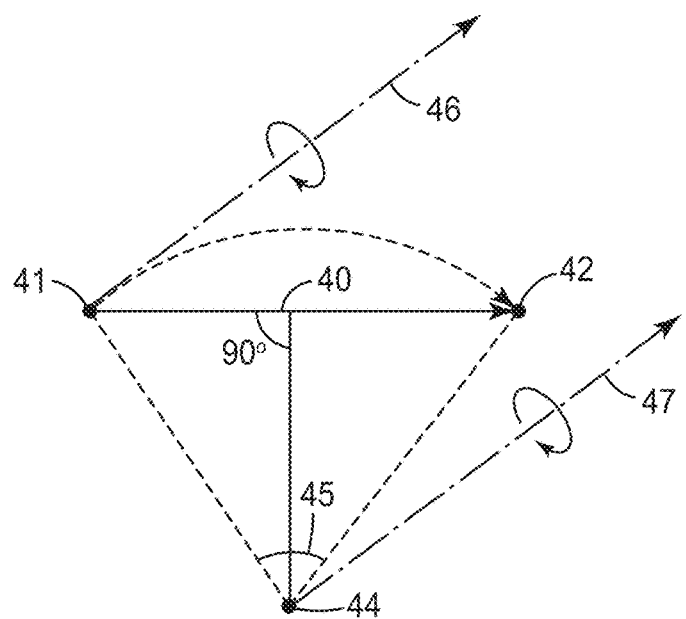
FIG. 6 illustrates converting a translation vector with a rotation component to a pure rotation axis.

In the particular case of human mandible movement, the possible movements are mechanically conditioned to the condyle and fossa, acting as a "ball joint." This particular condition of "ball joint" movements permits describing any of those mandible movements (coming from the different poses) as a unique pure rotation (without translation) instead of the combination of a rotation plus a translation (as any generic movement requires). FIG. 6 illustrates a method for converting a translation vector plus the rotation component to a pure rotation around a unique axis in this particular "ball joint" movement of the condyle in the fossa.

Figure 7:
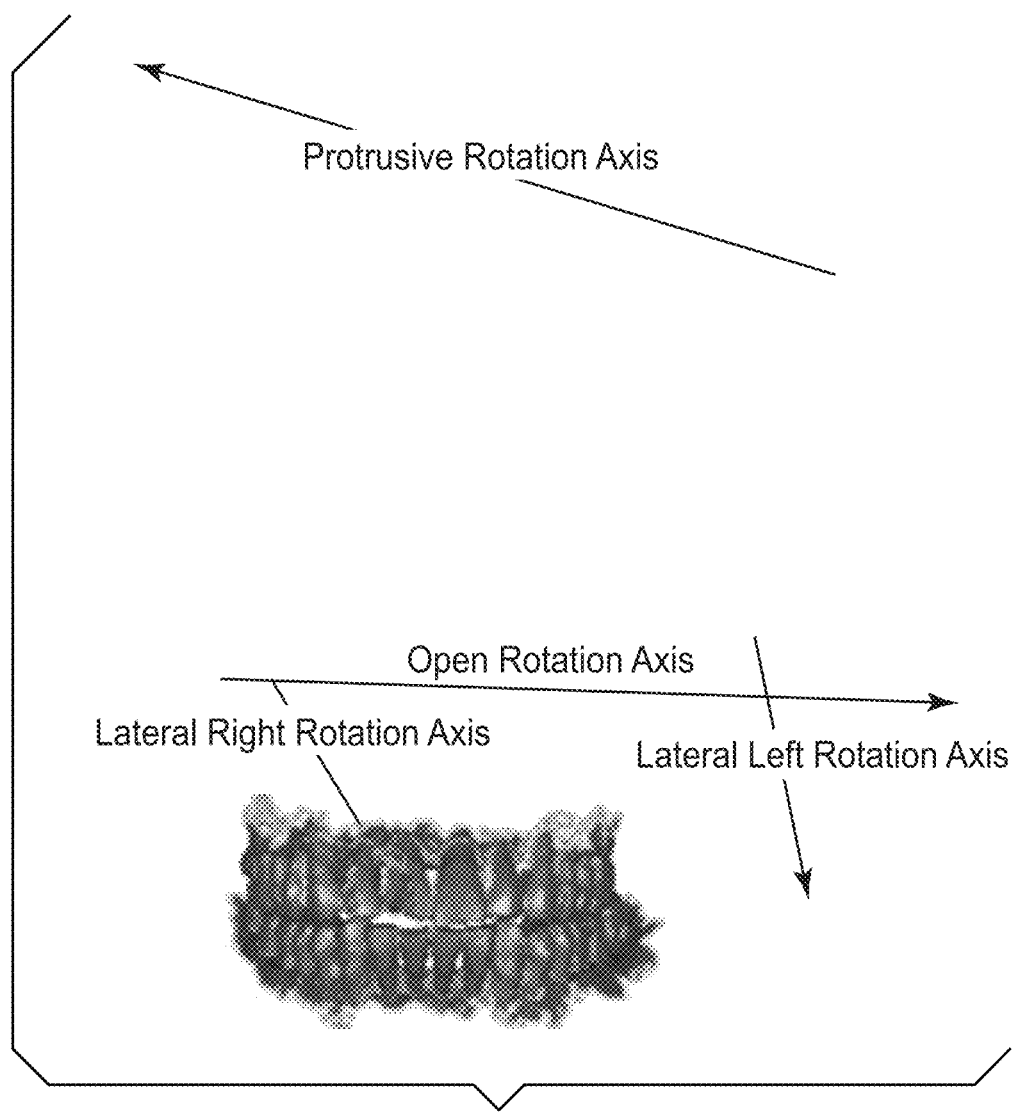
FIG. 7 illustrates a digital 3D model illustrating articulation motions in a virtual model.

The scans and poses illustrated in FIGS. 4 and 5, along with the registration of the pose scans with a reference scan, provides for a translation vector 40 between start point 41 (origin of coordinates of mandible 3D object) and 42 (end point of that initial point of the mandible), and a rotation vector 46 component referred to as the original rotation axis. The translation vector 40 with the rotation vector 46 is equivalent to a pure rotation axis 47 passing through a computed point 44. In this way, the movement from the original pose to any given pose that was originally described as the combination of a rotation (angle 45) around axis 46 and a translation through translation vector 40 (from point 41 to point 42) NOW can be described as a unique pure rotation (rotation angle 45) around axis 47. This transformation is performed to convert the translation vectors and original rotation axes for each of the mandible positions (open, right, left, forward) to pure rotation axes for each of those positions, and the combined movement of a mandible around those four pure rotation axes provides the virtual articulation model, as illustrated in FIG. 7. In particular, this virtual articulation model uses the pure rotation axes illustrated in FIG. 7 to simulate the comprehensive mandibular movement as a combination of four simple mandibular motions between the bite pose scans as follows: open to closed; protrusive or forward to closed; lateral right forward to closed; and lateral left forward to closed.

Input Scans

Figure 8:
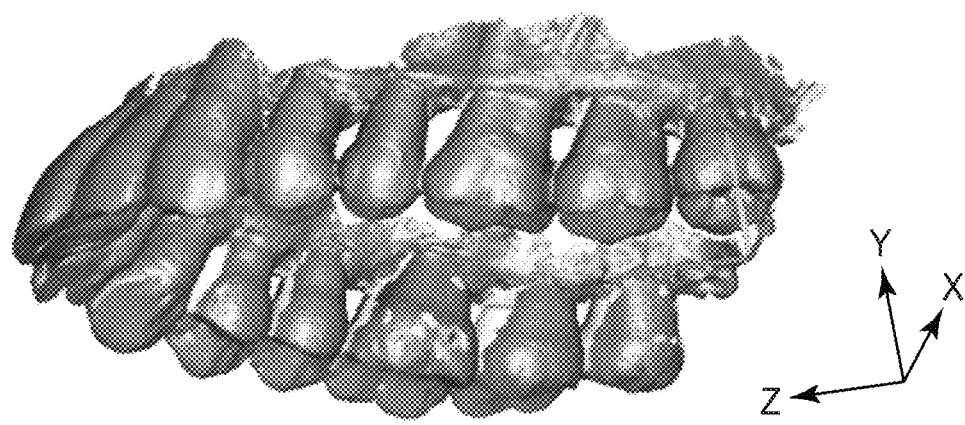
FIG. 8 illustrates a digital 3D model of a maxillary arch.
Figure 9:
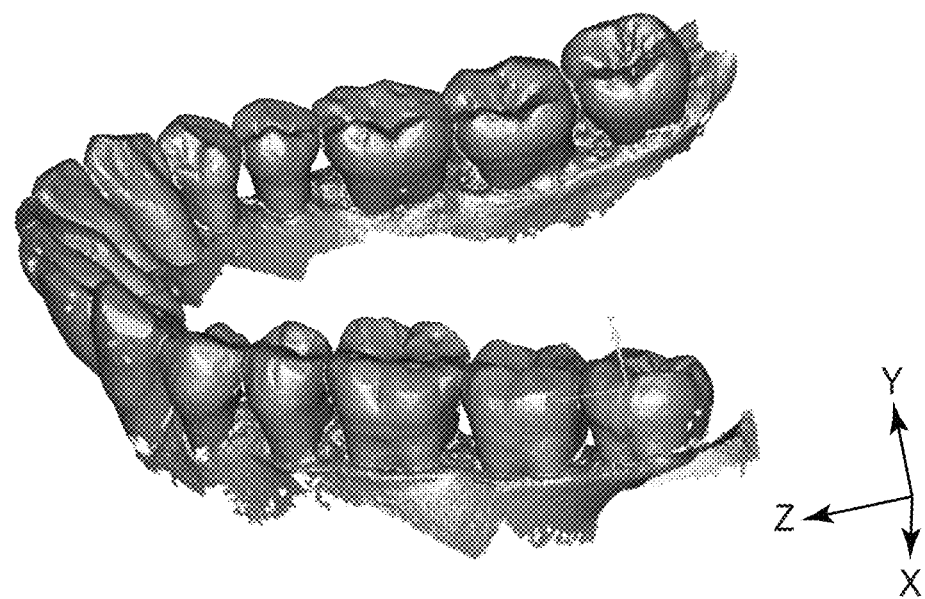
FIG. 9 illustrates a digital 3D model of a mandibular arch.
Figure 10:
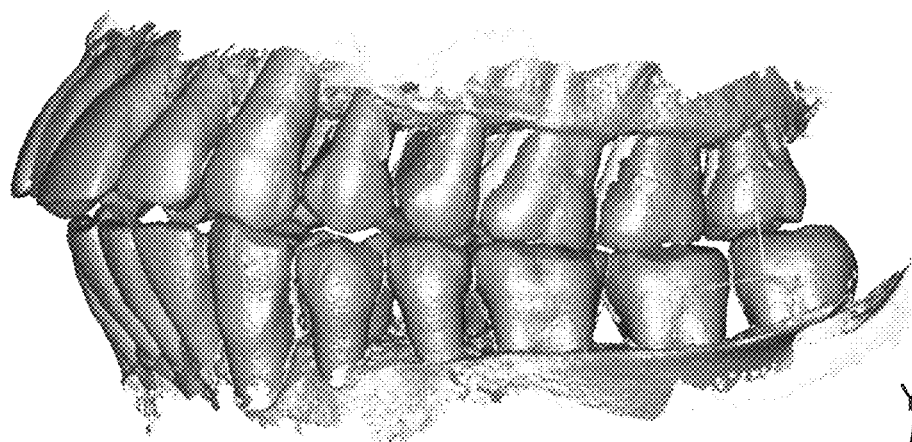
FIG. 10 illustrates a digital 3D model of a closed bite pose.
Figure 11:
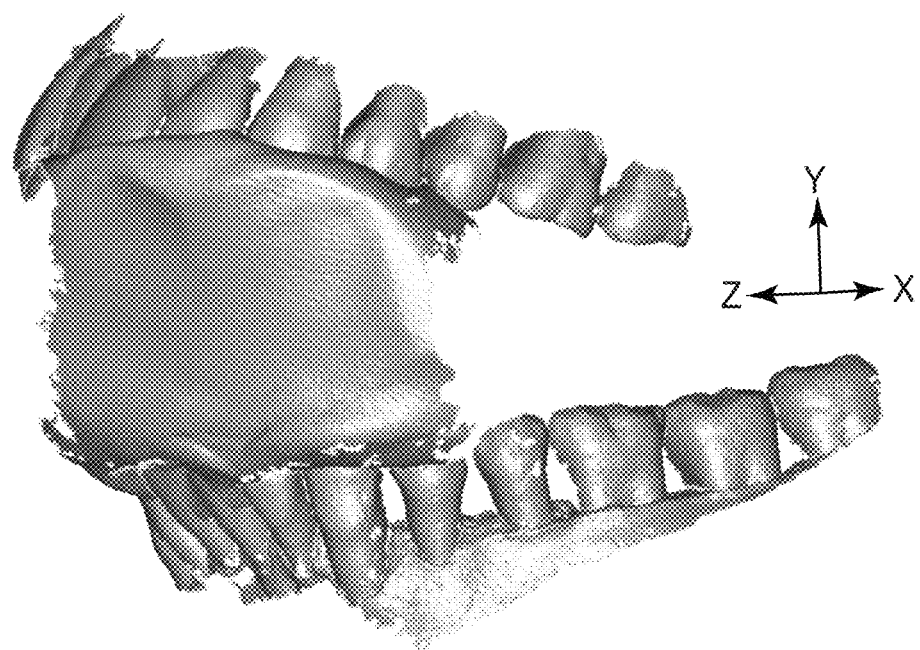
FIG. 11 illustrates a digital 3D model of an open bite pose.
Figure 12:
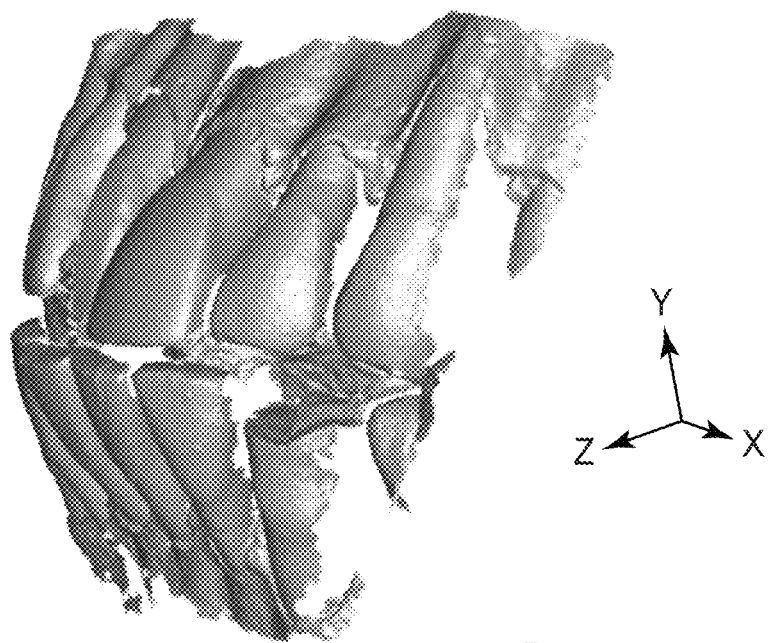
FIG. 12 illustrates a digital 3D model of a protrusive (forward) bite pose.
Figure 13:
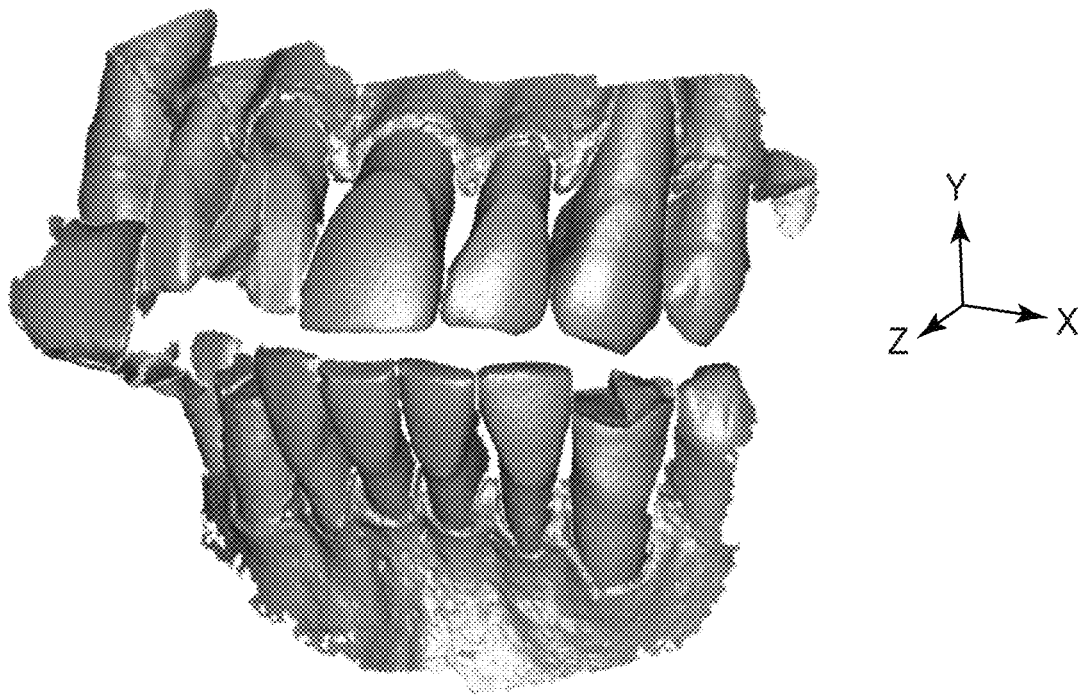
FIG. 13 illustrates a digital 3D model of a left lateral bite pose.
Figure 14:
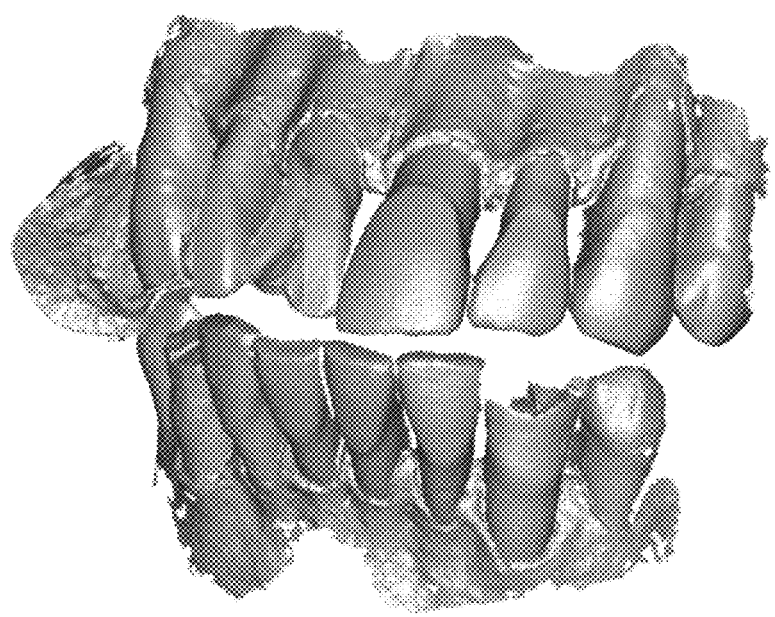
FIG. 14 illustrates a digital 3D model of a right lateral bite pose.

The input data for generating a virtual articulation model includes seven intra-oral scans: a scan of the maxillary arch as illustrated in FIG. 8; a scan of the mandibular arch as illustrated in FIG. 9; a scan of the closed (centric, maximum inter-cuspidation) bite pose as illustrated in FIG. 10; a scan of the open bite pose, including an intermediary object to maintain the spatial relationship between the arches as illustrated in FIG. 11; a scan of the protrusive (forward) bite pose as illustrated in FIG. 12; a scan of the left lateral bite pose as illustrated in FIG. 13; and a scan of the right lateral bite pose as illustrated in FIG. 14. The digital 3D models or scans in FIGS. 8-14 can be obtained using an intra-oral scanner as described above and are illustrative of such input scans from the same patient. These scans can also possibly be obtained from a library of scans of a patient, or by scanning impressions or castings of the patient's teeth. The input scans preferably include the full arches but could possibly include only partial arches. The bite pose scans can include scans of extreme bite poses to the limits of such movement or, alternatively, scans of bite poses with significant displacement but not to the limit. In the lateral poses, the working side condyle must be in the rear position, rotating as a "ball joint" without any translation. The other condyle will be translated forward, but the scan should be done without any overall protrusion of the mandible. Scanning with the working side condyle in rotation only enables accurate motion representation by the pure rotation model.

Calculating Best Fit Registrations and Transforms

The individual mandibular and maxillary arch scans are registered with each of the bite pose scans. Registration includes finding the best geometric fit of the arch scan (mandibular or maxillary) with a bite scan and is an application of known algorithms for registration of two or more 3D models. For example, one approach for registering 3D data is a known algorithm called Iterative-Closest Point (ICP) matching. Other registration algorithms are disclosed in U.S. Patent Application Publication No. 2016/0004811, which is incorporated herein by reference as if fully set forth.

Registration of the two arches with a bite scan enables computing a 3D transform defining the spatial relationship between the two arch scans in the pose of that bite scan. The maxilla is considered fixed in a default coordinate space. The mandible and maxilla are considered to be rigid objects that can move in space but cannot change size. Each bite registration transform therefore describes the relative translation (position) and rotation (orientation) of the mandible to the maxilla.

Figure 15:
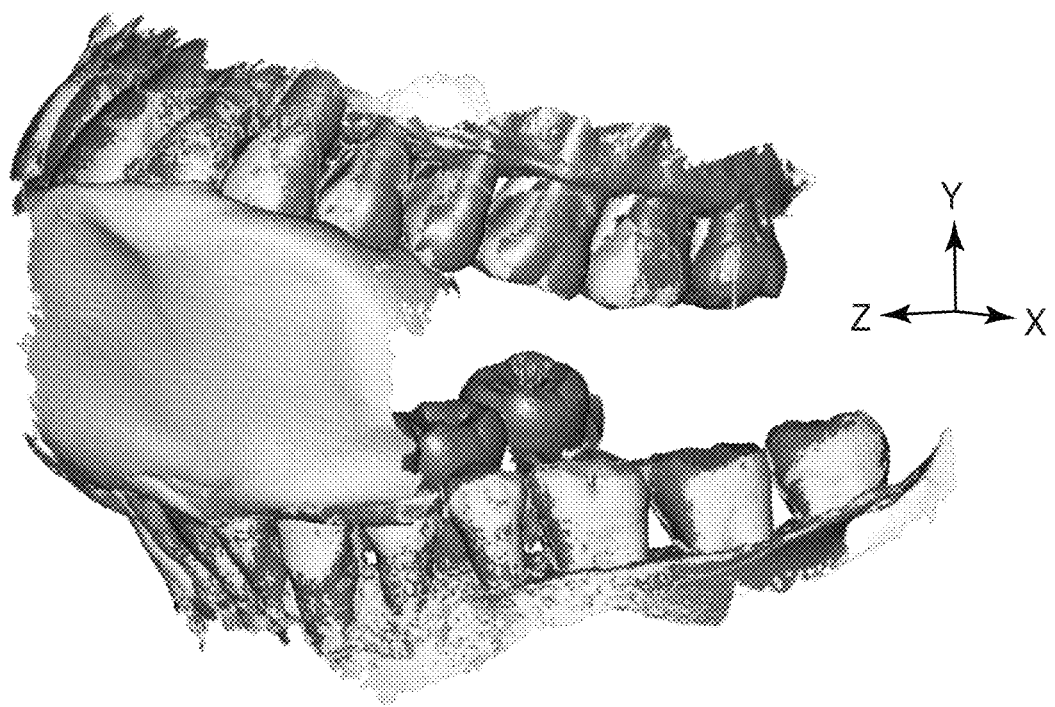
FIG. 15 illustrates a digital 3D model of an open pose.
Figure 16:
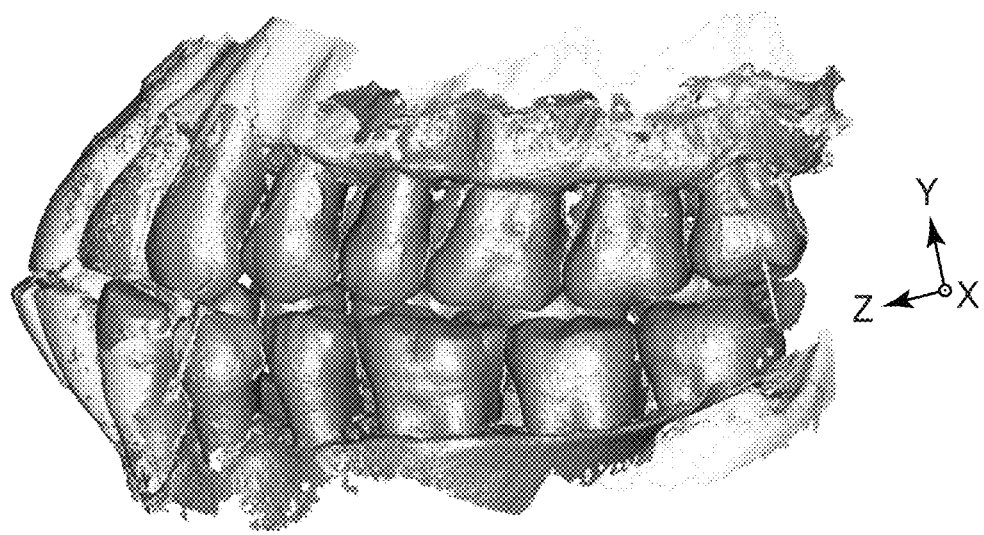
FIG. 16 illustrates a digital 3D model of a protrusive pose.
Figure 17:
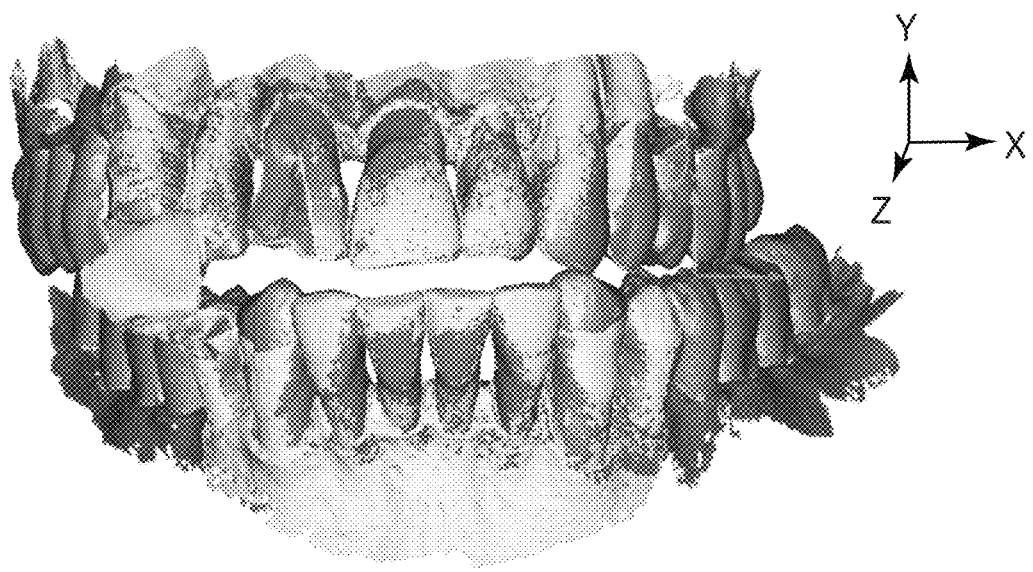
FIG. 17 illustrates a digital 3D model of a left lateral pose.
Figure 18:
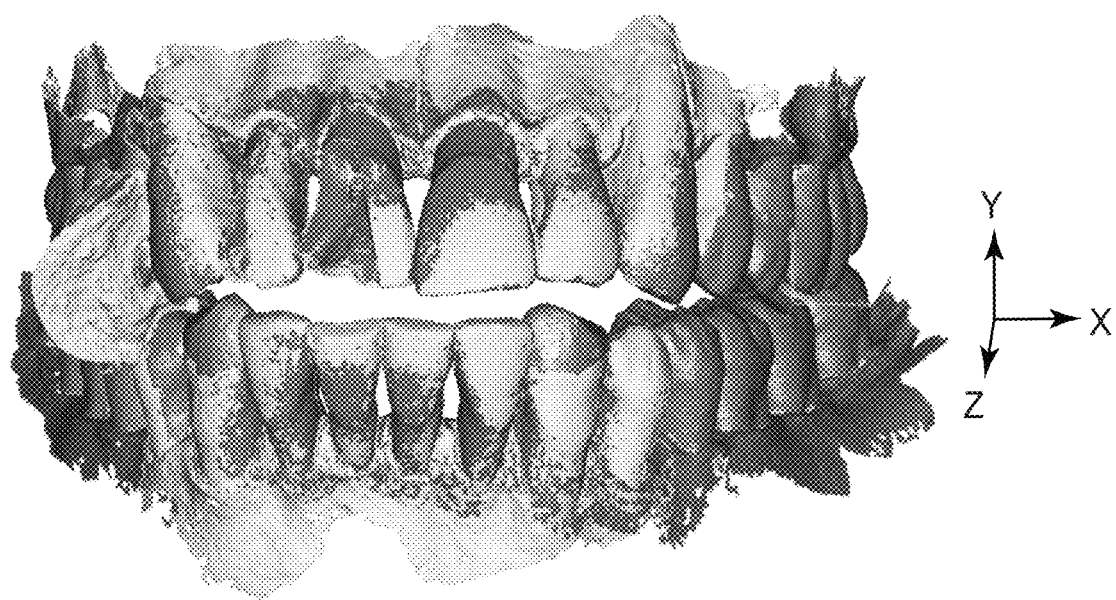
FIG. 18 illustrates a digital 3D model of a right lateral pose.

Bite registrations are found for the bite scans described above. The transformation matrix is found for the mandible in the following poses: open pose as illustrated in FIG. 15; protrusive pose as illustrated in FIG. 16; left lateral pose as illustrated in FIG. 17; and right lateral pose as illustrated in FIG. 18. These bite scans of these poses, shown in FIGS. 15-18, are registered with the closed bite pose scan in this example or with a different scan as the reference scan.

Each transformation can be expressed as a 3D matrix containing the rotation and translation of the mandible relative to the maxilla with the rotation expressed as three rotations around the three coordinate axes (X, Y, and Z), a.k.a. Euler angles. Other equivalent expressions exist such as an axis-angle rotation plus a translation vector, or a quaternion rotation plus a translation vector. The transforms can be stored in a database, for example, with the rotation stored as a 3×3 submatrix and the translation stored as three elements of a column in the matrix. These transforms are then used to determine the corresponding pure rotation axes.

In some embodiments for the registration, the maxillary arch can be comprised of any recognizable portion of the maxillary dental arch, maxillary alveolar process, palate, skull, or head, excluding the mandible. In particular, the calculated pure rotation axes can be physically linked to the temporomandibular joint (rear of fossa and upper eminentia angle) morphology. As a result, the virtual articulation obtained at a given time can be re-called at any further time for the same patient by registering a time-fix part of the oral cavity (the palate). When registering the palate in a new scan with the palate of a previous scan for the same patient and which contains the virtual articulation information, these calculated pure rotation axes will be accurately transferred to the new scan. A patient's virtual articulation information can thus be transferred from one scan to another for the patient.

Equivalent Pose and Interpolation Representations

Once the registration transforms are known, interpolations between the closed pose and other individual bite poses can be used to move the mandible. Rigid transforms are typically decomposed into rotation and translation components that are interpolated separately, then recombined into an interpolated transform. Numerous types of interpolations are possible. Linear interpolation of the two components would result in a straight path through space with an accompanying rotation. Higher order interpolations or table based interpolations could be used to model physically derived motion paths. The method described herein uses an alternate representation of the pose transforms that uses only a rotation component to effect the motion, which when interpolated follows a circular arc through space instead of a straight line. This alternate representation more closely approximates the swivel behavior of natural jaw motion. This representation is referred to as a "pure rotation" and provides for an equivalent or corresponding rotation to a transform containing both translation and rotation, since the pure rotation results in the same end pose.

Described below are the calculations required for finding this equivalent or corresponding pure rotation representation. First the method finds the pure rotation axis and the rotation angle, then it finds one point of the pure rotation axis to determine the pure rotation axis position such that the pure rotation attains the desired end pose without an additional translation.

Finding the original rotation axis and rotation angle involves the following. Rigid body motion can be described as an orientation (3×3 rotation matrix, which represents the rotation around the three coordinate axes) plus a translation (translation vector which represents a vector starting at the coordinate space origin and ending at the equivalent point).

Let R be the 3×3 rotation matrix of a given motion, with its components labeled as:

$$R = \begin{bmatrix} n_x & o_x & a_x \\ n_y & o_y & a_y \\ n_z & o_z & a_z \end{bmatrix}$$

The rotation angle is calculated as:

$$\phi = \tan^{-1} \frac{\sqrt{(o_z - a_y)^2 + (a_x - n_z)^2 + (n_y - o_x)^2}}{n_x + o_y + a_z - 1}$$

The original rotation axis is calculated as:

$$r_x = \frac{o_z - a_y}{2\sin\phi}$$

$$r_y = \frac{a_x - n_z}{2\sin\phi}$$

$$r_z = \frac{n_y - o_x}{2\sin\phi}$$

Finding a point on the pure rotation axis involves the following. A pure rotation requires defining the line equation of the pure rotation axis including its position. The geometry above produces an original rotation axis that passes through the coordinate space origin, changing the orientation of the object being transformed but ignoring the translational component of the original transform. The desired pure rotation requires a pure rotation axis parallel to the original rotation axis at some offset such that rotation around the pure axis, without a translation operation, will achieve the same result as the original transform (including the translation component).

Figure 19:
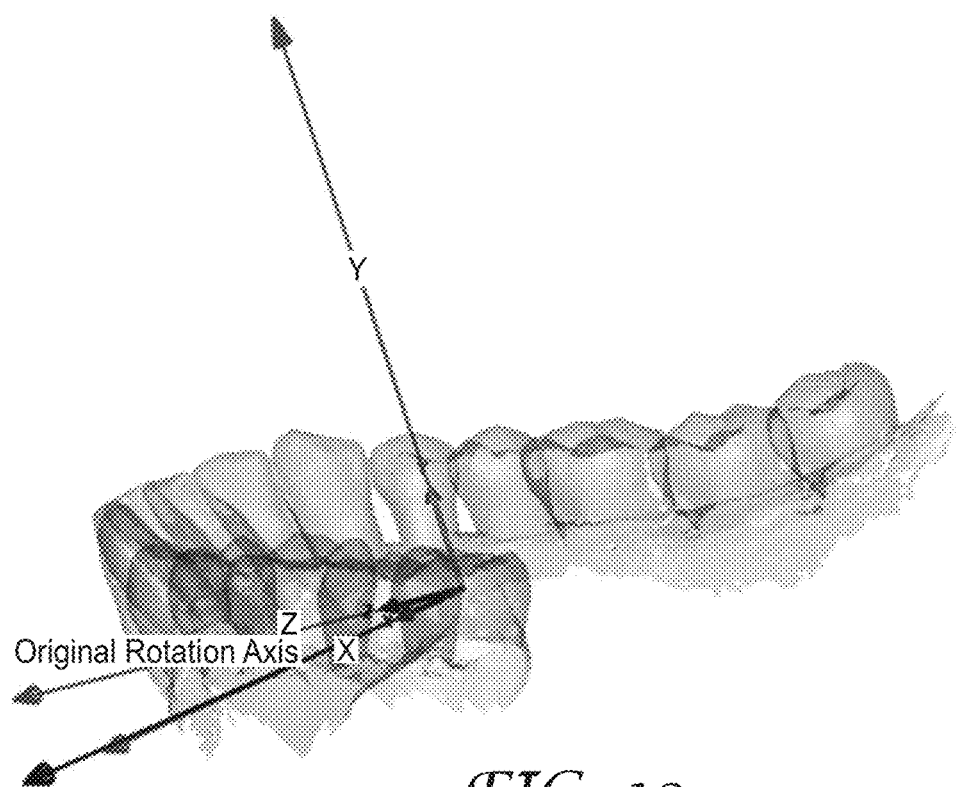
FIG. 19 illustrates an original rotation axis in a digital 3D model.
Figure 20:
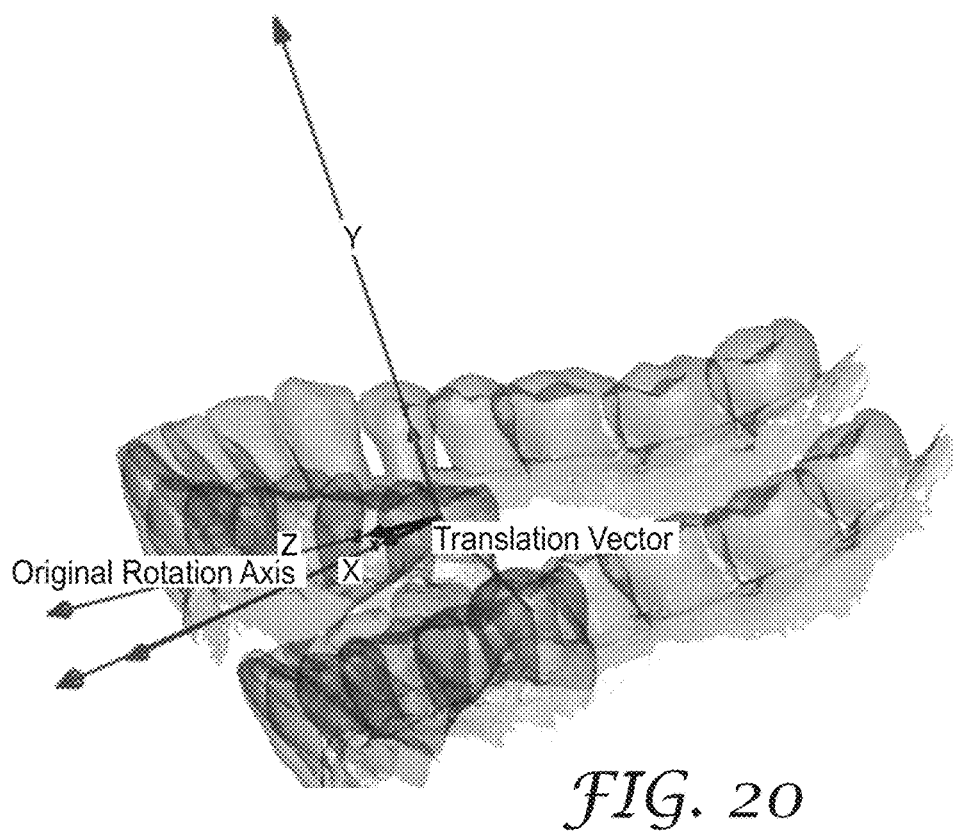
FIG. 20 illustrates a translation vector in a digital 3D model.
Figure 21:
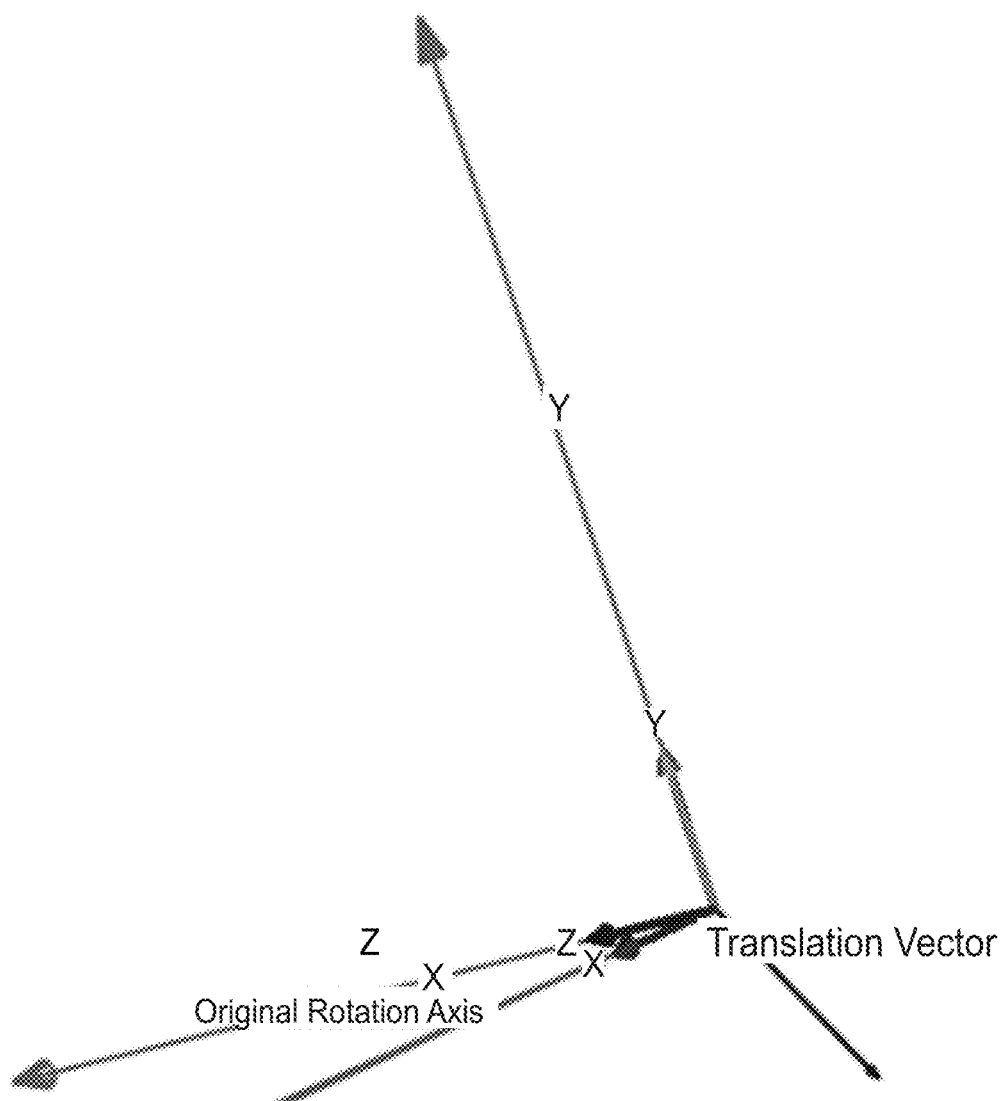
FIG. 21 illustrates rotation and translation vectors.

FIG. 19 represents the coordinate system (X, Y, Z) and the original rotation axis obtained in the previous section. FIG. 20 shows the original coordinate system, the transformed mandible and the translation vector obtained in the previous section. From the vectorial perspective, the situation is illustrated in FIG. 21.

A key to finding one point of the pure rotation axis is taking into account the following conditions. The pure rotation axis will be parallel to the original rotation axis that passes through the origin. Defining a line (named Auxiliary Line in FIGS. 22-24) starting at the midpoint of the translation vector and perpendicular to it, will intersect the pure rotation axis. The angle rotated to meet that Auxiliary Line will be half of the rotated angle. By definition, the original rotation axis will always be perpendicular to the translation vector. This vectorial composition is illustrated in FIG. 22.

Figure 22:
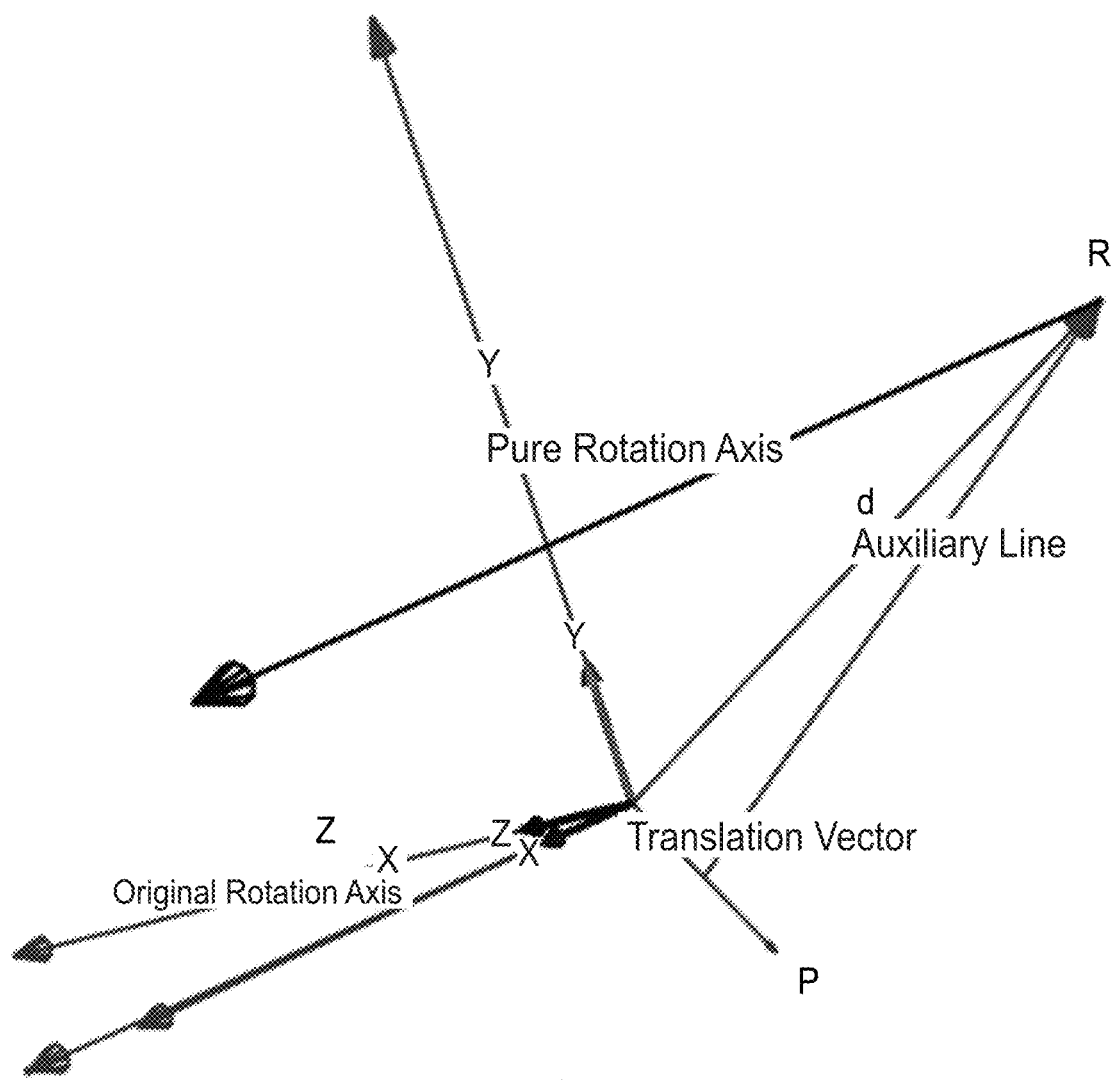
FIG. 22 illustrates a vectorial composition.
Figure 23:
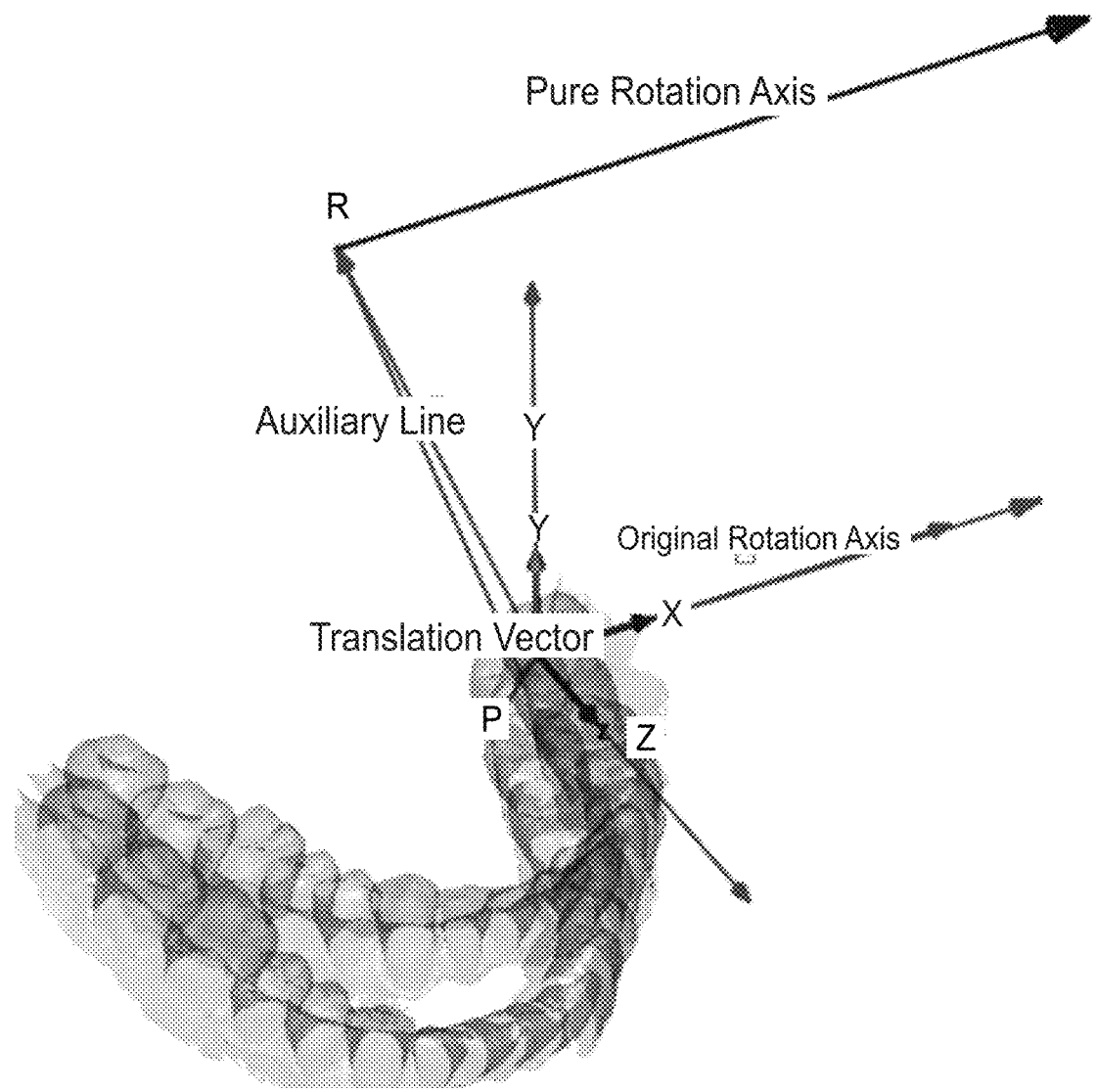
FIG. 23 illustrates vectors with a digital 3D model.
Figure 24:
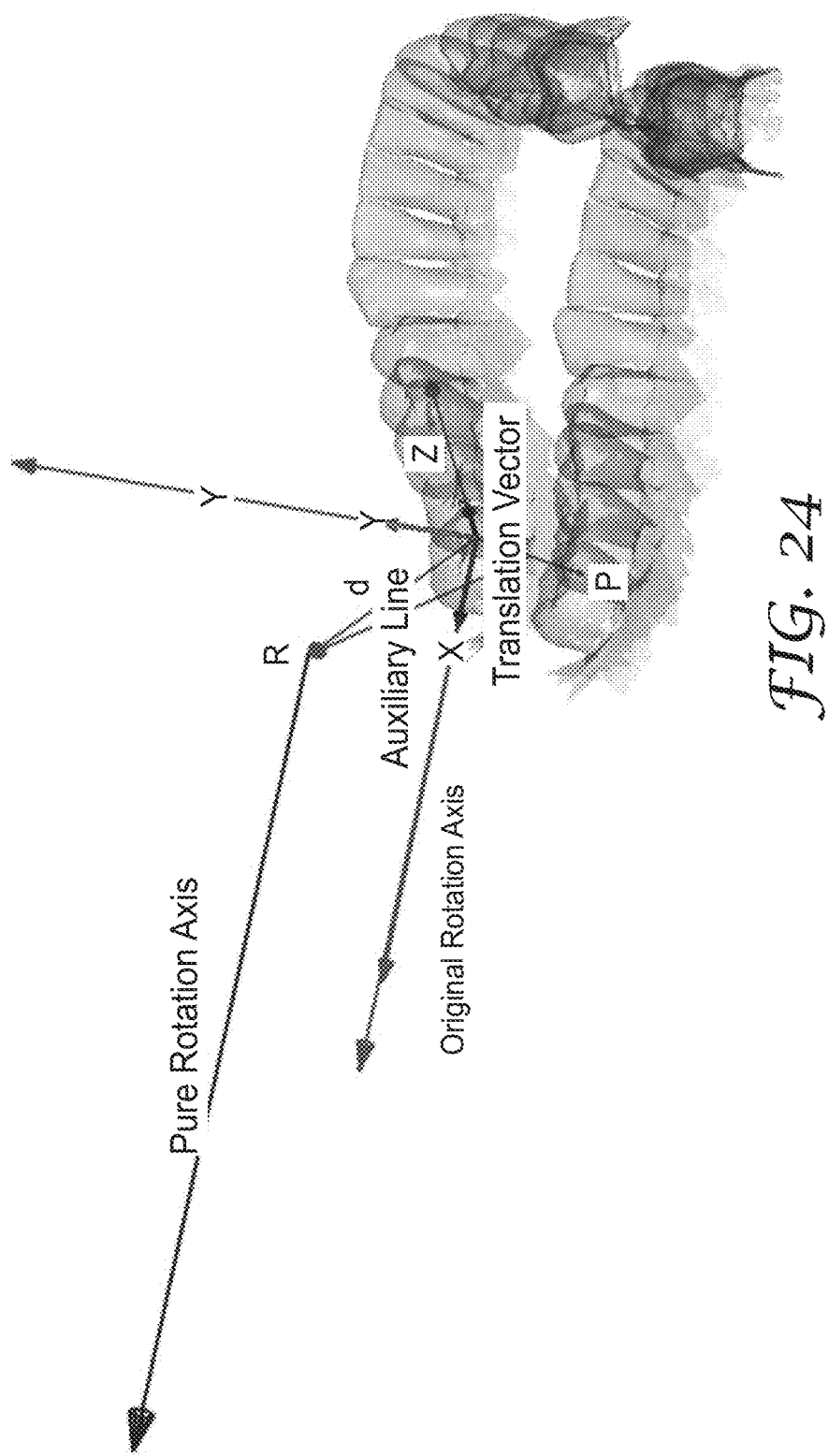
FIG. 24 illustrates vectors with a digital 3D model.

The pure rotation axis, identified as Pure Rotation Axis in FIGS. 22-24, will intersect the Auxiliary Line at point R. The distance "d" (from origin to point R) will be exactly the rotation radius from the origin. The angle between line d and the Auxiliary Line will be half of the pure rotation angle calculated before (considering that the Auxiliary Line was built starting at the middle of the translation vector). For another illustration of the vectors, lines, and points involved, see FIGS. 23 and 24 including the objects (original and moved) from different perspectives.

According to this situation, the equations are:

Point $R$: $(X_R, Y_R, Z_R)$

Point $P$: $(X_P, Y_P, Z_P)$

Point $P_0$ (midpoint of translation vector): $(X_0, Y_0, Z_0)$, defined as $$X_0 = \frac{X_P}{2}$$

$$Y_0 = \frac{Y_P}{2}$$

$$Z_0 = \frac{Z_P}{2}$$

$u_1$ (unitary vector in the direction of the Auxiliary Line): $(u_{1x}, u_{1y}, u_{1z})$ Rotation angle: $\phi$ The parameter $u_1$ is obtained as the normalized vector product between the translation vector and original rotation axis (both of them available from the previous step).

The Auxiliary Line equation could be written as:

$$X_R = X_0 + \lambda u_{1x}$$

$$Y_R = Y_0 + \lambda u_{1y}$$

$$Z_R = Z_0 + \lambda u_{1z}$$

Applying basic trigonometry (where O is the origin point):

$$\frac{\overline{OP_0}}{d} = \sin\frac{\phi}{2}$$

So the rotation radius can be expressed as:

$$d = \frac{\overline{OP_0}}{\sin\frac{\phi}{2}} \quad (1)$$

But distance "d" can be expressed as well based on the points O and R as follows:

$$d^2 = X_R^2 + Y_R^2 + Z_R^2 = (X_0 + \lambda u_{1x})^2 + (Y_0 + \lambda u_{1y})^2 + (Z_0 + \lambda u_{1z})^2 = (u_{1x}^2 + u_{1y}^2 + u_{1z}^2)\lambda^2 + 2(X_0 u_{1x} + Y_0 u_{1y} + Z_0 u_{1z})\lambda + (X_0^2 + Y_0^2 + Z_0^2) \quad (2)$$

But, $u_{1x}^2 + u_{1y}^2 + u_{1z}^2 = 1$, provided $u_1$ is a unitary vector $X_0 u_{1x} + Y_0 u_{1y} + Z_0 u_{1z}$ is the *dot* product $\overrightarrow{OP_0} \cdot \overrightarrow{u_1}$ and is equal to 0, provided $\overrightarrow{OP_0}$ is normal to $\overrightarrow{u_1}$ $X_0^2 + Y_0^2 + Z_0^2 = \overrightarrow{OP_0}^2$ So combining equations (1) and (2), the following is an equation for determining $\lambda$:

$$\lambda^2 + \overline{OP_0}^2 - \left(\frac{\overline{OP_0}}{\sin\frac{\phi}{2}}\right)^2 = 0$$

this is, $$\lambda^2 = \frac{\overline{OP_0}^2}{\left(\tan\frac{\phi}{2}\right)^2}$$

So, finally, the method obtains the value of $\lambda$ that determines the point R on the pure rotation axis as:

$$\boxed{\lambda = \frac{\overline{OP_0}}{\tan\frac{\phi}{2}}}$$

Finally, the point R can be expressed as $$X_R = X_0 + \frac{\overline{OP_0}}{\tan\frac{\phi}{2}} u_{1x}$$

$$Y_R = Y_0 + \frac{\overline{OP_0}}{\tan\frac{\phi}{2}} u_{1y}$$

$$Z_R = Z_0 + \frac{\overline{OP_0}}{\tan\frac{\phi}{2}} u_{1z}$$

Figure 25:
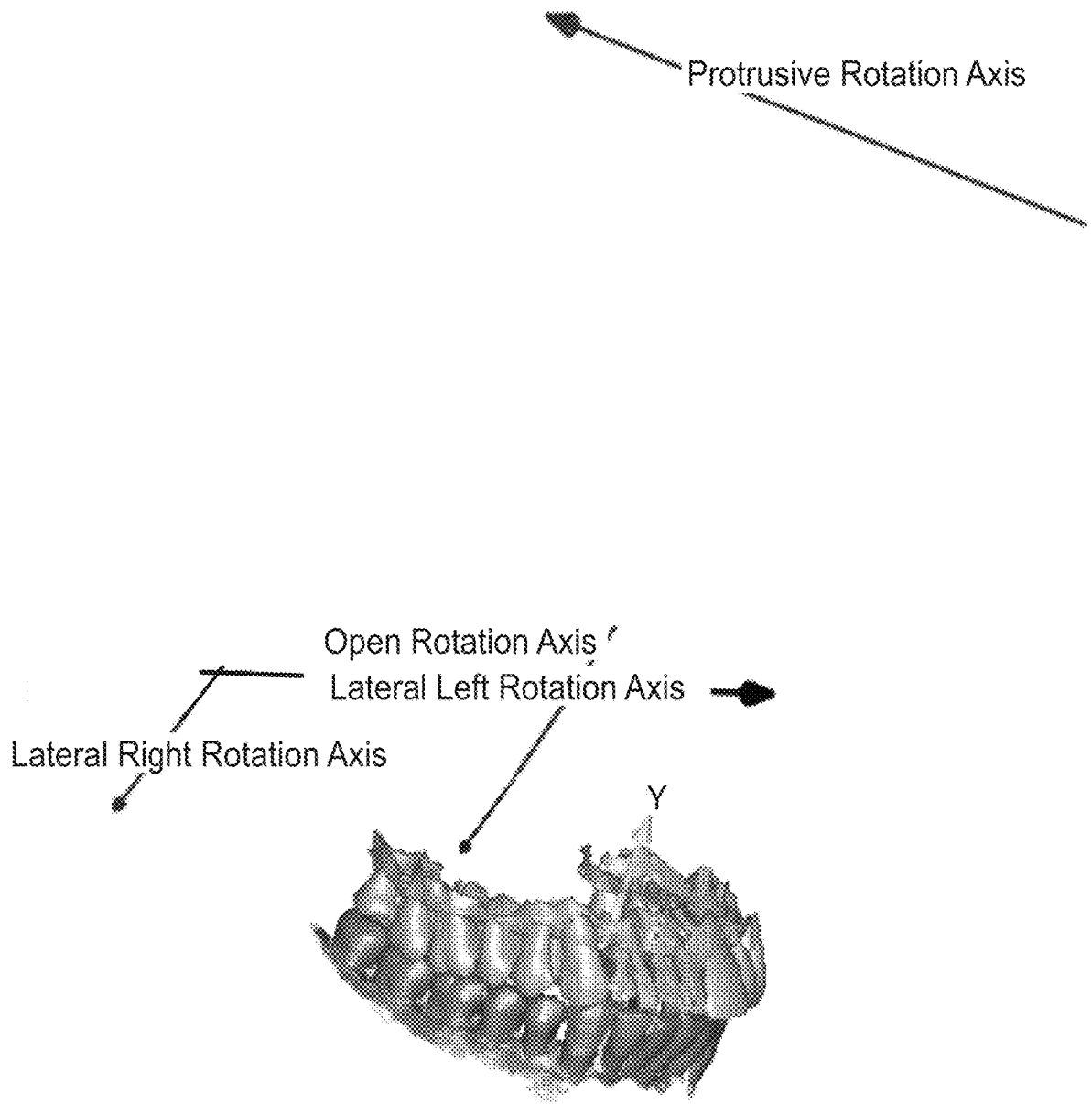
FIG. 25 illustrates a digital 3D model with four different axes which animate the mandible model for virtual articulation.

This procedure is repeated to obtain a rotation point for each of the pure rotation axes of the four poses. The pure rotation axes obtained from this procedure for the four different axes which animate the mandible model are represented in FIG. 25. The rotation points and corresponding rotation angles for the four pure rotation axes can be stored in a database, for example.

Composite Motion via Combining and Constraining Individual Transforms

The full range of motion of the mandible can be composed from the individual transforms at varying states of interpolation. Constraining a given interpolation parameter dependent on the interpolation parameters of other motions can help limit the range of motion to a more faithful representation of physical reality.

Each of the five bite registrations, by virtue of representing extreme or significant excursions of the jaw, establish constraints of the mandibular motion in some directions. For example, the mandible cannot move more to the left than the extreme left bite pose, nor can the mandible close more than the closed bite registration. Therefore, interpolation between (and not extrapolation beyond) the individual extreme poses and the closed pose as an exemplary reference provides one set of constraints. An example convention for this method is that an interpolation parameter of 0 represents the closed pose and a parameter of 1 represents a bite pose of one of the other bite scans. Parameters between 0 and 1 represent an intermediate pose between the two scanned extremes.

Figure 26:
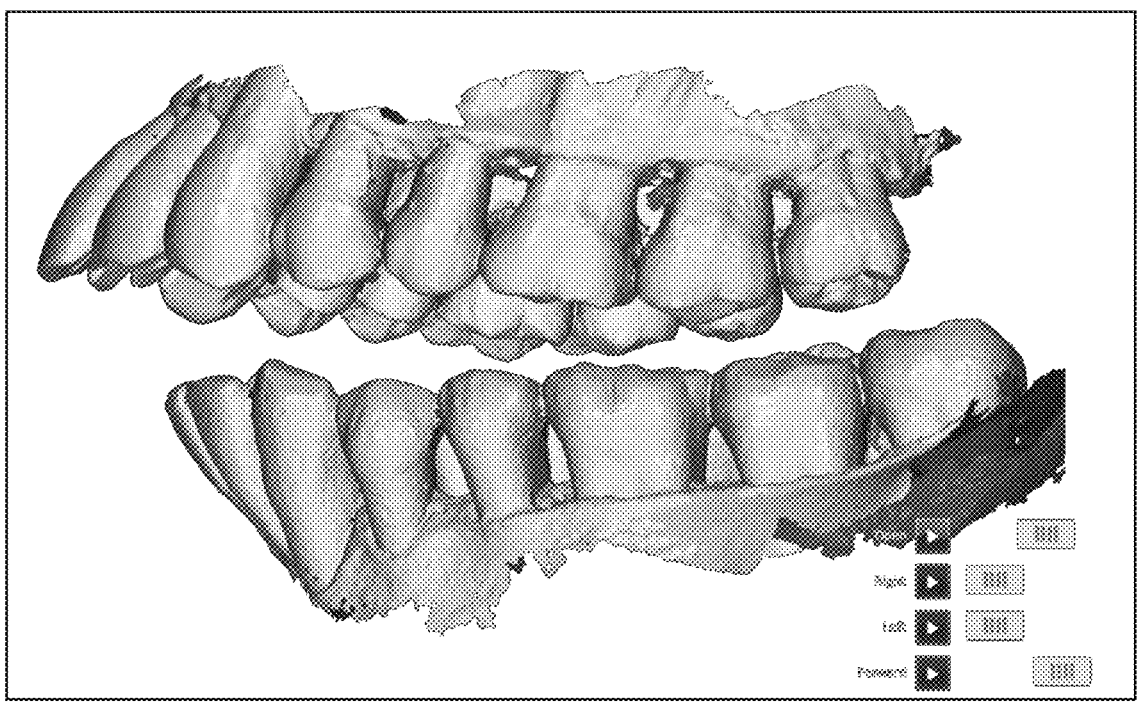
FIG. 26 is a diagram of a user interface for applying a virtual articulation model.

The comprehensive virtual articulation model includes a combination of the four interpolated poses which can be expressed as a set of four interpolation parameters. An example is shown in the user interface of FIG. 26 with the displayed sliders (Open, Right, Left, Forward) in the lower right corresponding to the four interpolation parameters. This user interface can be displayed on display device 16. A user can adjust the displayed sliders using input device 18 (e.g., a cursor-control device) to view the corresponding motion of the displayed virtual articulation model. Adjusting the sliders causes rotation of the corresponding pure rotation between the two end points for the selected type of movement or pose. The sliders also have an animation mode to achieve continuous motion, including multiple sliders animating simultaneously with phase differences determined by the user to simulate different complex motion cycles. Aside from sliders, a touch screen can be used for example, to move the displayed representation of the mandibular arch amongst combinations of the four poses.

To constrain the range of motion to match physical reality, additional limits on the interpolation values can be imposed. For example, the left and right motions cannot be used simultaneously. This can be expressed as limiting the two respective interpolation parameters so that at most one of them is non-zero. Rotation values can be restricted to positive values—right axis is valid only for lateral right movement; left axis is valid only for lateral left movement. For combining a lateral rotation with an open rotation, the open rotation axis must be rotated in the space according to the lateral rotation. In other words, the open-close hinge must rotate relative to the laterally rotated mandible just as does the real human mandible. Additional types of constraints can also be utilized. More nuanced physically-based constraints based on human motion studies can be added. Collision detection between the arches during motion can be used to prevent interpenetration between the arches, for example of opposing tooth surfaces.

The invention claimed is:

1. A computer-implemented method for displaying a user interface comprising a view of virtual articulation from dental scans on an electronic display device, wherein:
   a portion of the user interface displays a virtual articulation model of a person's intra-oral structure,
   the virtual articulation model is based upon digital 3D models of a plurality of different bite poses of the person's maxillary arch and mandibular arch, including a pure rotation axis of the mandibular arch with respect to the maxillary arch, and
   the plurality of different bite poses includes digital 3D models for a closed bite pose, an open bite pose, a protrusive bite pose, a left lateral bite pose, and a right lateral bite pose.

2. The method of claim 1, further comprising a plurality of icons displayed in the user interface for user control input comprising open, right, left, and forward motion of the displayed virtual articulation model.

3. The method of claim 1, wherein the user interface is displayed on a touch screen for receiving user control input comprising open, right, left, and forward motion of the displayed virtual articulation model.

4. The method of claim 1, wherein the digital 3D models of the plurality of different bite poses are acquired via an intra-oral scanner.

5. The method of claim 1, wherein the digital 3D models of the plurality of different bite poses are acquired via Cone Beam Computed Tomography scanning.

6. The method of claim 1, wherein the digital 3D models of the plurality of different bite poses are acquired via Magnetic Resonance Imaging.

7. A computer-implemented method for displaying a user interface comprising a view of virtual articulation from dental scans on an electronic display device, wherein:
   a portion of the user interface displays a virtual articulation model of a person's intra-oral structure with possible movement of the person's mandibular arch relative to the person's maxillary arch,
   the possible movement of the person's mandibular arch relative to the person's maxillary arch is based upon digital 3D models of a plurality of different bite poses of the person's maxillary arch and mandibular arch, and
   the possible movement of the person's mandibular arch relative to the person's maxillary arch includes a full range of motion of the mandibular arch.

8. The method of claim 7, wherein the plurality of different bite poses includes digital 3D models for a closed bite pose, an open bite pose, a protrusive bite pose, a left lateral bite pose, and a right lateral bite pose.

9. The method of claim 7, further comprising a plurality of icons displayed in the user interface for user control input comprising open, right, left, and forward motion of the displayed virtual articulation model.

10. The method of claim 7, wherein the user interface is displayed on a touch screen for receiving user control input comprising open, right, left, and forward motion of the displayed virtual articulation model.

11. The method of claim 7, wherein the digital 3D models of the plurality of different bite poses are acquired via an intra-oral scanner.

12. The method of claim 7, wherein the digital 3D models of the plurality of different bite poses are acquired via Cone Beam Computed Tomography scanning.

13. The method of claim 7, wherein the digital 3D models of the plurality of different bite poses are acquired via Magnetic Resonance Imaging.

14. A computer-implemented method for displaying a user interface comprising a view of virtual articulation from dental scans on an electronic display device, wherein:

a portion of the user interface displays a virtual articulation model of a person's intra-oral structure with possible movement of the person's mandibular arch relative to the person's maxillary arch, the possible movement of the person's mandibular arch relative to the person's maxillary arch is based upon digital 3D models of a plurality of different bite poses of the person's maxillary arch and mandibular arch, and the digital 3D models of the plurality of different bite poses includes digital 3D models for a closed bite pose and other individual bite poses.

15. The method of claim 14, further comprising a plurality of icons displayed in the user interface for user control input comprising open, right, left, and forward motion of the displayed virtual articulation model.

16. The method of claim 14, wherein the user interface is displayed on a touch screen for receiving user control input comprising open, right, left, and forward motion of the displayed virtual articulation model.

17. The method of claim 14, wherein the digital 3D models of the plurality of different bite poses are acquired via an intra-oral scanner.

18. The method of claim 14, wherein the digital 3D models of the plurality of different bite poses are acquired via Cone Beam Computed Tomography scanning.

19. The method of claim 14, wherein the digital 3D models of the plurality of different bite poses are acquired via Magnetic Resonance Imaging.

* * * * *